United States Patent [19]

Wagner et al.

[11] Patent Number: 5,795,707
[45] Date of Patent: Aug. 18, 1998

[54] PHOTOGRAPHIC SILVER HALIDE MATERIAL

[75] Inventors: Klaus Wagner, Bergisch Gladbach; Günter Helling; Torsten Groth, both of Odenthal; Winfried Joentgen, Köln, all of Germany

[73] Assignee: Agfa-Gevaert, Germany

[21] Appl. No.: 802,713

[22] Filed: Feb. 19, 1997

[30] Foreign Application Priority Data

Mar. 1, 1996 [DE] Germany ............ 196 07 852.0

[51] Int. Cl.$^6$ .................... G03C 1/047; G03C 1/015
[52] U.S. Cl. .................... 430/569; 430/567; 430/628; 430/642
[58] Field of Search .................... 430/642, 567, 430/569, 628

[56] References Cited

U.S. PATENT DOCUMENTS

| | | | |
|---|---|---|---|
| 2,699,391 | 1/1955 | Mueller et al. | 430/609 |
| 4,315,072 | 2/1982 | Fox et al. | 430/628 |
| 5,371,180 | 12/1994 | Groth et al. | 528/363 |
| 5,506,335 | 4/1996 | Uhr et al. | 528/322 |
| 5,543,490 | 8/1996 | Groth et al. | 528/328 |
| 5,580,712 | 12/1996 | Keevert, Jr. et al. | 430/569 |
| 5,594,077 | 1/1997 | Groth et al. | 525/451 |
| 5,610,255 | 3/1997 | Groth et al. | 526/304 |

*Primary Examiner*—Mark F. Huff
*Attorney, Agent, or Firm*—Connolly & Hutz

[57] ABSTRACT

A photographic silver halide material having a support and at least one layer which is deposited thereon and which contains a polypeptide, at least 90 mole % of which consists of structural units of formula I.

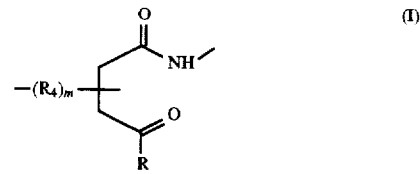

where
R represents OH, $NH_2$, $NHR_1$, $NR_1R_2$, NH— or $NR_1$—
$R_1$, $R_2$ represent a hydrocarbon radical, which is optionally substituted,
$R_4$ represents NH or N—, and
m represents 0 or 1,
wherein the bond between two structural units of formula I is always an —N—C bond and m is equal to 1 in 2 to 35% of the structural units of formula I, is characterised by improved photographic properties.

11 Claims, No Drawings

PHOTOGRAPHIC SILVER HALIDE MATERIAL

This invention relates to a photographic silver halide material, in which a synthetic polyamide is used in at least one layer.

Photographic silver halide materials contain silver halide crystals, which are usually precipitated in the presence of gelatine, as their light-sensitive constituent. The gelatine also constitutes the binder for the silver halide crystals in the finished material.

The gelatine has diverse effects on silver halide grain formation and on the photographic properties of the material. For this reason, the gelatine has been varied time after time in order to obtain properties which are the optimum, depending on the use, and which are reproducible—which cannot be taken for granted for a natural product such as gelatine.

It has not been possible hitherto to fulfil all these requirements. Improvements are thus necessary in the twinning of silver halide crystals, in the growth of plate-like silver halide crystals (tab grains), in ripening and in spectral sensitisation, in order to arrive at improved photographic products.

The object of the present invention was partially to replace gelatine by other media with which this problem can be solved.

Surprisingly, it has now been found that considerable improvements can be achieved if certain synthetic polyamides, which are essentially based on a short chain aminodicarboxylic acid as the monomer, are used in at least one layer of the photographic material.

The present invention therefore relates to a photographic silver halide material having a support and at least one layer which is deposited thereon and which contains a polypeptide, at least 90 mole % of which consist of structural units of formula I,

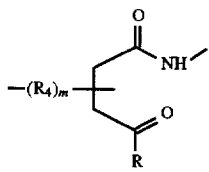
(I)

where

R represents OH, NH$_2$, NHR$_1$, NR$_1$R$_2$, NH— or NR$_1$—

R$_1$, R$_2$ represent a hydrocarbon radical, which is optionally substituted,

R$_4$ represents NH or N—, and m represents 0 or 1, wherein the bond between two structural units of formula I is always an —N—C bond and m is equal to 1 in 2 to 35% of the structural units of formula I.

If R is NH— or NR$_1$— or R$_4$ N—, this results in branched or crosslinked products.

More than 98 mole % of the polypeptide preferably consists of structural units of formula I. The linkage between the structural units of formula I may be different, so that the following dipeptides result, for example, which can be detected qualitatively but which cannot be determined quantitatively with exactitude:

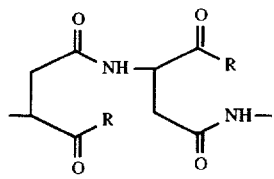
(β-peptide linkage)
R = OH, m = 0

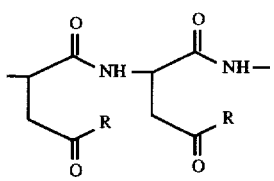
(α-peptide linkage)
R = OH, m = 0

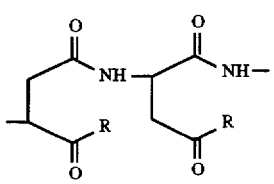
(α,β-peptide linkage)
R = OH, m = 0

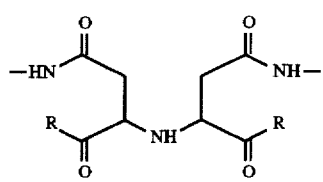
(β-imine linkage)
R = OH, m = 1*

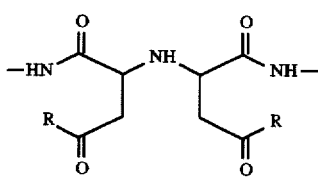
(α-imine linkage)
R = OH, m = 1*

(* for one structural unit)

The imine nitrogen atoms may likewise be the centre of a branched structure, for example in the following form:

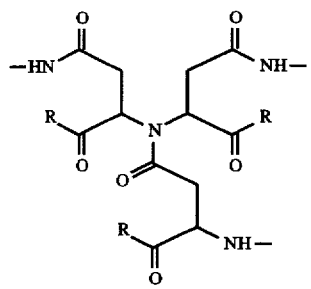

Moreover, the polypeptides may contain the following structural units:

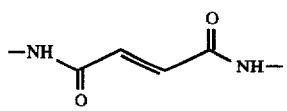

and contain the following structures as terminal groups:

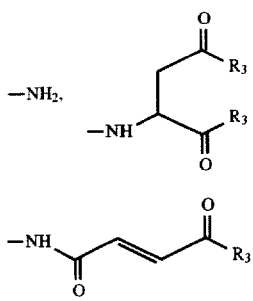

where $R_3$ represents OH, $NH_2$, $NHR_1$ or $NR_1R_2$.

The polypeptides can be obtained thermally from aspartic acid (J. Org. Chem. 26, 1084 (1961) or DE 4 023 463) or are obtained by the condensation of maleic acid or maleic anhydride and ammonia or an amine (DE 3 626 672, 4 244 031, 4 305 368, 4 319 044, EP 650 995 or U.S. Pat. No. 5,371,180).

If R represents OH, the polypeptides may be present as free acids or as salts, e.g. as alkali or ammonium salts.

They have an average molecular weight (weight average) of 1000 to 100,000, preferably 1000 to 10,000.

The layer of photographic material which contains the polypeptide is preferably a silver halide emulsion layer. This layer preferably contains the polypeptide in an amount of 0.02 to 1.5 g/m$^2$.

The polypeptide is preferably used in admixture with gelatine, the amount of polypeptide being 1 to 100% by weight of the amount of gelatine in the layer concerned.

The photographic silver halide material may be a black and white or a colour photographic material.

Examples of colour photographic materials include colour negative films, colour reversal films, colour positive films, colour photographic paper, colour reversal photographic paper, or colour-sensitive materials for the colour diffusion transfer process or for the silver colour-bleaching process.

Photographic materials consist of a support on which at least one light-sensitive silver halide emulsion layer is deposited. Thin films and foils are particularly suitable as supports. A review of support materials and of the auxiliary layers which are deposited on the front and back thereof is presented in Research Disclosure 37254, Part 1 (1995), page 285.

Colour photographic materials usually contain at least one red-sensitive, one green-sensitive and one blue-sensitive silver halide emulsion layer in each case, and optionally also contain intermediate layers and protective layers.

Depending on the type of photographic material, these layers may be arranged differently. This will be illustrated for the most important products:

Colour photographic films such as colour negative films and colour reversal films comprise, in the following sequence on the support, 2 or 3 red-sensitive, cyan-coupling silver halide emulsion layers, 2 or 3 green-sensitive, magenta-coupling silver halide emulsion layers and 2 or 3 blue-sensitive, yellow-coupling silver halide emulsion layers. Layers which have the same spectral sensitivity differ as regards their photographic sensitivity, and the less sensitive partial layers are generally disposed nearer the support than are the more highly sensitive partial layers.

Between the green-sensitive and blue-sensitive layers there is usually a yellow filter layer which prevents blue light from reaching the layers situated below it.

Possible forms of different layer arrangements and their effects on photographic properties are described in J. Int. Rec. Mats., 1994, Vol. 22, pages 183–193.

Colour photographic paper, which is generally less light-sensitive than a colour photographic film, usually comprises, in the following sequence on the support, a blue-sensitive, yellow-coupling silver halide emulsion layer, a green-sensitive, magenta-coupling silver halide emulsion layer and a red-sensitive, cyan-coupling silver halide emulsion layer; the yellow filter layer may be omitted.

Variations in the number and arrangement of the light-sensitive layers can be made in order to obtain certain results. For example, all the high-sensitivity layers can be combined to form one layer stack and all the low-sensitivity layers can be combined to form another layer stack in a photographic film, in order to increase the film speed (DE 2 530 645).

The essential constituents of the photographic emulsion layers are binders, silver halide grains and colour couplers.

Information on suitable binders is to be found in Research Disclosure 37254, Part 2 (1995), page 286.

Information on suitable silver halide emulsions, and on the production, ripening, stabilisation and spectral sensitisation thereof, including suitable spectral sensitisers, is to be found in Research Disclosure 37254, Part 3 (1995), page 286 and in Research Disclosure 37038, Part XV (1995), page 89.

Photographic materials which have a speed of response suitable for cameras usually contain silver bromide-iodide emulsions, which may optionally also contain small proportions of silver chloride. Photographic copier materials contain either silver chloride-bromide emulsions comprising up to 80 mole % AgBr or silver chloridebromide emulsions comprising more than 95 mole % AgCl.

Information on colour couplers is to be found in Research Disclosure 37254, Part 4 (1995), page 288, and in Research Disclosure 37038, Part II (1995), page 80. The maximum absorption of the dyes formed from the couplers and from the colour developer oxidation product is preferably within the following ranges: yellow couplers 430 to 460 nm, magenta couplers 540 to 560 nm, cyan couplers 630 to 700 nm.

In order to improve film speed, granularity, sharpness and colour separation, compounds are frequently used in colour photographic films which, on their reaction with the developer oxidation product release compounds which are photographically active, e.g. DIR couplers, which release a development inhibitor.

Information on compounds such as these, particularly on couplers, is to be found in Research Disclosure 37254, Part 5 (1995), page 290, and in Research Disclosure 37038, Part XIV (1995), page 86.

The colour couplers, which are mostly hydrophobic, and other hydrophobic constituents of the layers also, are usually dissolved or dispersed in high boiling organic solvents. These solutions or dispersions are then emulsified in an aqueous solution of a binder (usually a gelatine solution), and after drying the layers are present as fine droplets (0.05 to 0.8 µm diameter) in the layers.

Suitable high boiling organic solvents, methods of introducing a photographic material into the layers, and other methods of introducing chemical compounds into photographic layers, are to be found in Research Disclosure 37254, Part 6 (1995), page 292.

The non-light-sensitive intermediate layers, which are generally disposed between layers of different spectral sensitivity, may contain media which prevent the unwanted diffusion of developer oxidation products from one light-sensitive layer into another light-sensitive layer with a different spectral sensitisation.

Suitable compounds (white couplers, scavengers or EOP scavengers) are to be found in Research Disclosure 37254, Part 7 (1995), page 292 and in Research Disclosure 37038, Part III (1995), page 84.

In addition, the photographic material may contain compounds which absorb UV light, optical brighteners, spacers, filter dyes, formalin scavengers, light stabilisers, antioxidants, $D_{Min}$ dyes, additives for improving the stability of the dyes, of the couplers and of the whiteness and for reducing colour fogging, plasticisers (latices), biocides and others.

Suitable compounds are to be found, in Research Disclosure 37254, Part 8 (1995), page 292 and in Research Disclosure 37038, Parts IV, V, VI, VII, X, XI and XIII (1995), page 84 et seq.

The layers of colour photographic materials are usually hardened, i.e the binder which is used, preferably gelatine, is crosslinked by suitable chemical methods.

Suitable hardener substances are to be found in Research Disclosure 37254, Part 9 (1995), page 294 and in Research Disclosure 37038, Part XII (1995), page 86.

After their image-by-image exposure, colour photographic materials are processed by various methods corresponding to their character. Details of the procedures used and the chemicals required therefor are published, together with examples of materials, in Research Disclosure 37254, Part 10 (1995), page 294, and in Research Disclosure 37038, Parts XVI to XXII (1995), page 95 et seq.

The polyamide which is to be used according to the invention is known and can be produced at elevated temperatures from maleic anhydride and ammonia in aqueous medium (EP 650 995).

The present invention also relates to a method of producing silver halide emulsions, characterised in that the precipitation of the silver halide, particularly the precipitation of the nuclei, is effected in the presence of a polypeptide according to the invention.

In particular, precipitation of the nuclei is effected in the presence of 3 to 100 g of the polypeptide per mole of silver halide.

In this connection, the precipitation of nuclei is to be considered as the first section of a multi-stage crystal precipitation process.

In a precipitation process in which the next stage immediately follows the precipitation of nuclei, the final point of the precipitation of nuclei is to be understood as the point in time after which the number of particles remains substantially constant.

EXAMPLES

Examples 1 to 3 (preparation of the polypeptides)

Example 1

500 g (3.76 mole) D,L-aspartic acid were polymerised as a layer 0.5–1.0 cm thick on a drying plate in a drying oven, at a reaction space temperature of 244° C. and under a vacuum of 400 mbar whilst passing a stream of nitrogen over the material. 379 g (97.5% theoretical) of polysuccinimide were obtained. 250 g polysuccinimide were suspended in 500 g water and mixed with 103.2 g (2.58 mole) NaOH. The reaction mixture was heated at 105° C. for 7 hours, whereupon a total of about 3 kg of ammoniacal liquor were continuously distilled off. The corresponding amount was continuously replaced by fresh water, by metered addition from a dropping funnel. After the distillation, 790 g were obtained of a 42.2% by weight of a solution of a Na salt of a polypeptide, with the following elemental analysis data: C=14.8% by weight, N=4.1% by weight, and a molecular weight of 5300 (weight average, determined by GPC). m was equal to 1 in 11% of the structural units of formula I.

Example 2

The $NH_4$ salt of maleic acid (5 kg/hour, melting point 171° C.) was metered into a stainless steel sheet metal screw heated to 175° C. (supplied by Lurgi, "Selfcleaner" type, length 0.9 m; o.d. 0.1 m; rotational speed 15 revs/min). In the course of this procedure, the starting material melted within a short time and water of reaction escaped. A fluid reaction melt was first formed, which transformed in the course of the polymerisation into a highly viscous reaction mass and then into a solid. A beige polysuccinimide, ranging from powder to flakes, was obtained (3.54 kg/hour, 91.4% of the theoretical yield with respect to carbon). The saponification number was 10 mmole NaOH/g polysuccinimide.

Alkaline hydrolysis was effected based on the saponification number. Thus 900 g polysuccinimide were suspended in 2000 ml water, mixed with 720 g of 50% by weight aqueous sodium hydroxide solution, and hydrolysed at 100°–105° C. Ammoniacal liquor was distilled off in the course of this procedure.

The solution of the Na salt of the polypeptide was concentrated and the product was dried. 1349 g were obtained (C=31.1% by weight; N=8.9% by weight; =100% theoretical yield with respect to carbon). The average molecular weight was 2500 ($M_w$ from GPC).

m was equal to 1 in 22% of the structural units of formula I.

Example 3

Molten maleic anhydride (20 kg/hour, 100° C.) and 50% by weight aqueous ammonia solution (9.7 kg/hour, 5° C., 40% excess) were thoroughly mixed with each other in a jet mixer comprising a smooth jet nozzle (o.d.=0.35 mm).

The crude product was produced in a subsequent continuous thermal polymerisation stage at a pressure of 13–14 bar in a helical coil type reactor (length=9.5 m; o.d.=15 mm) heated to 200° C.

The crude product was introduced into a boiler (2 bar, containing water) and was continuously mixed with 5% by weight aqueous NaOH solution (20 kg/hour). The crude product solution which was produced had a pH of 5.0 and a saponification number of 3.7 mmole NaOH/g solution.

Based on the measured saponification number, 189 kg of the crude product solution were mixed with 0.7 kmole NaOH and sufficient water and were boiled for 2 hours at 130° C. in the pressure vessel. Ammoniacal liquor was subsequently distilled off. A further 0.03 kmole NaOH and water were added and the mixture was boiled for 0.5 hours at 130° C. After distilling off the residual ammoniacal liquor, 210 kg were obtained of a 45% by weight solution of the sodium salt of a polypeptide with a total nitrogen content of 85% theoretical with respect to carbon ($C_4$ units) and a molecular weight of 2100 ($M_w$ from GPC).

m was equal to 1 in 21% of the structural units of formula I.

Examples 4 to 8 (production of silver halide emulsions)

Example 4 (EM-1, comparison)

An aqueous solution comprising 12 g of inert bone gelatine and 73 g KBr in 2.5 liters of water was placed in a 10 liter reaction vessel. 0.6 moles of $AgNO_3$ were fed as a 1.5 molar solution to this batch at a constant metered rate over a period of 4 minutes at a temperature of 25° C.

The pH was then adjusted to 6.0 and the reaction temperature was increased to 75° C., a further 54 g of inert bone gelatine was fed in as a 20% by weight gelatine gel together with 0.25 mole KBr as a 1 molar solution, and an Ostwald ripening of 20 minutes' duration was carried out.

Thereafter, a further 0.98 mole AgNO₃ and 0.88 mole KBr, together with 0.05 mole KI, were each added as 1 molar solutions over a period of 35 minutes with an increasing rate of metered addition, the final rate of addition being twice as great as the initial rate of addition.

After an interval of 10 minutes, a further 0.24 mole AgNO₃ and 0.19 mole KI, together with 0.3 mole KBr, were each fed in as 1 molar solutions over a period of 5 minutes at a constant rate of addition.

After a further 10 minute interval, 2 mole AgNO₃ and 2 mole KBr were again fed in as 1 molar solutions over a period of 40 minutes and at a constant rate of addition.

Thereafter the emulsion was cooled, flocculated by acidification with the addition of a flocculent, and the flocculate was redispersed, after it had been repeatedly washed out, with the addition of inert bone gelatine. The emulsion obtained in this manner (EM-1) had a total iodide content of 6.3 mole % and a weight ratio of gelatine to silver of 0.25 (with respect to AgNO₃). The average grain diameter was 0.7 μm, with a grain size coefficient of variation of 30%. The proportion of tabular crystals amounted to about 50% of the projected area of the emulsion and the aspect ratio of these tabular crystals was 4 to 5 (evaluation from electron microscope photographs).

Example 5 (EM-2, according to the invention)

EM 2 was produced by the procedure used for EM 1, except that the batch contained 12 g of the polypeptide according to Example 3 instead of 12 g of inert bone gelatine in the first step.

The average grain diameter was 0.82 μm, with a grain size coefficient of variation of 20%. The proportion of tabular crystals amounted to 80% of the projected area and the aspect ratio of the tabular crystals was 6.

Example 6 (EM-3, according to the invention)

EM 3 was produced by the procedure used for EM 1, except that the batch contained 16 g of the polypeptide according to Example 1 instead of 12 g of inert bone gelatine in the first step.

The average grain diameter was 0.73 μm, with a grain size coefficient of variation of 21%. The proportion of tabular crystals amounted to 85% of the projected area and the aspect ratio of these tabular crystals was 8.

Example 7 (EM-4, according to the invention)

EM 4 was produced by the procedure used for EM 1, except that the batch contained 14 g of the polypeptide according to Example 1 instead of 12 g of inert bone gelatine in the first step.

The average grain diameter was 0.74 μm, with a grain size coefficient of variation of 22%. The proportion of tabular crystals amounted to 85% of the projected area and the aspect ratio of these tabular crystals was 7.

Example 8 (EM-5, according to the invention)

EM 5 was produced by the procedure used for EM 1, except that the batch contained 16 g of the polypeptide according to Example 2 instead of 12 g of inert bone gelatine in the first step.

The average grain diameter was 0.72 μm, with a grain size coefficient of variation of 19%. The proportion of tabular crystals amounted to 87% of the projected area and the aspect ratio of these tabular crystals was 8.

Examples 5 to 8 show that when a polypeptide according to the invention is used the proportion of tabular crystals increases considerably and the coefficient of variation of the grain size is significantly reduced.

We claim:

1. A photographic silver halide material which comprises a support and at least one layer which is deposited thereon and which contains a polypeptide, at least 90 mole % of which comprises structural units of formula I,

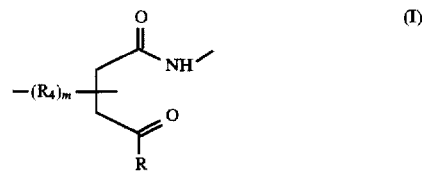

where
R represents OH, NH₂, NHR₁, NR₁R₂, NH— or NR₁—
R₁ and R₂ independently of one another represent a substituted or unsubstituted hydrocarbon radical,
R₄ represents NH or N—, and
m represents 0 or 1,
wherein the bond between two structural units of formula I is always an —N—C bond and m is equal to 1, in 2 to 35% of the structural units of formula I.

2. The photographic silver halide material according to claim 1, wherein the polypeptide has an average molecular weight (weight average) of 1000 to 100,000.

3. The photographic silver halide material according to claim 2, wherein the polypeptide has an average molecular weight (weight average) from 1,000 to 10,000.

4. The photographic silver halide material according to claim 3, wherein 0.02 to 1.5 g/m² of polypeptide are contained.

5. The photographic silver halide material according to claim 1, wherein the layer is a silver halide emulsion layer.

6. The photographic silver halide material according to claim 1, wherein more than 98 mol % of the polypeptide comprises of structural units of formula I.

7. The photographic silver halide material as claimed in claim 1, wherein said polypeptide is obtained from aspartic acid.

8. A method of producing a silver halide emulsion by a multi-stage crystal precipitation process having a first section and a final point of precipitation wherein the first section is the precipitation of silver halide nuclei which comprises precipitating the nuclei of silver halide in the presence of a polypeptide at least 90 mole % of which comprises structural units of formula I,

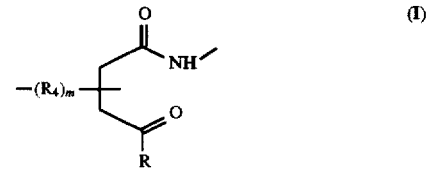

where
R represents OH, NH₂, NHR₁, NR₁R₂, NH— or NR₁—
R₁ and R₂ independently of one another represent a substitute or unsubstituted hydrocarbon radical,
R₄ represents NH or N—, and
m represents 0 or 1, wherein the bond between two structural units of formula I is always an —N—C bond and m is equal to 1, in 2 to 35% of the structural units of formula I, and the final point of the precipitation of nuclei is when the number of particles remains substantially constant.

9. The method according to claim 8, wherein 3 to 100 g polypeptide per mole of silver halide are used.

10. The method as claimed in claim 8, wherein at least 98 mol % of the polypeptide comprises structural units of formula I.

11. The method as claimed in claim 8, wherein said polypeptide is obtained from aspartic acid.

* * * * *